US012655108B2

(12) United States Patent
Wang

(10) Patent No.: US 12,655,108 B2
(45) Date of Patent: Jun. 16, 2026

(54) HETEROCYCLIC COMPOUND AS TYK2 PSEUDOKINASE DOMAIN INHIBITOR, SYNTHETIC METHOD, AND USE

(71) Applicant: ZHEJIANG WENDA PHARMA TECHNOLOGY LTD., Hangzhou (CN)

(72) Inventor: Nenghui Wang, Ningbo (CN)

(73) Assignee: ZHEJIANG WENDA PHARMA TECHNOLOGY LTD., Hangzhou (CN)

( * ) Notice: Subject to any disclaimer, the term of this patent is extended or adjusted under 35 U.S.C. 154(b) by 383 days.

(21) Appl. No.: 18/552,933

(22) PCT Filed: Mar. 28, 2022

(86) PCT No.: PCT/CN2022/083480

§ 371 (c)(1),
(2) Date: Sep. 28, 2023

(87) PCT Pub. No.: WO2022/206705

PCT Pub. Date: Oct. 6, 2022

(65) Prior Publication Data

US 2024/0182429 A1 Jun. 6, 2024

(30) Foreign Application Priority Data

Mar. 30, 2021 (CN) ......................... 202110343008.8

(51) Int. Cl.

| | |
|---|---|
| ***C07D 237/24*** | (2006.01) |
| ***A61K 31/444*** | (2006.01) |
| ***A61K 31/50*** | (2006.01) |
| ***A61K 31/501*** | (2006.01) |
| ***C07D 213/82*** | (2006.01) |
| ***C07D 401/12*** | (2006.01) |
| ***C07D 403/12*** | (2006.01) |

(52) U.S. Cl.

CPC .......... *C07D 237/24* (2013.01); *A61K 31/444* (2013.01); *A61K 31/50* (2013.01); *A61K 31/501* (2013.01); *C07D 213/82* (2013.01); *C07D 401/12* (2013.01); *C07D 403/12* (2013.01)

(58) Field of Classification Search

CPC .. C07D 237/24; C07D 401/12; C07D 403/12; A61K 31/444

See application file for complete search history.

(56) References Cited

U.S. PATENT DOCUMENTS 11,597,721 B2 * 3/2023 Xiao .................... C07D 513/04

FOREIGN PATENT DOCUMENTS

| | | | |
|---|---|---|---|
| CN | 104884454 | A | 9/2015 |
| CN | 111315737 | A | 6/2020 |
| CN | 111484480 | A | 8/2020 |
| WO | 2020159904 | A1 | 8/2020 |

OTHER PUBLICATIONS

International Search Report (with English translation) and Written Opinion issued in PCT/CN2022/083480, dated May 31, 2022, 16 pages provided.

Moslin et al., "Identification of N-Methyl Nicotinamide and N-Methyl Pyridazine-3-Carboxamide Pseudokinase Domain Ligands as Highly Selective Allosteric Inhibitors of Tyrosine Kinase 2 (TYK2)", J. Med. Chem. 2019, 62, 20, pp. 8953-8972, Publication Date:Jul. 17, 2019.

* cited by examiner

*Primary Examiner* — Kamal A Saeed

(74) *Attorney, Agent, or Firm* — HSML P.C.

(57) ABSTRACT

The present invention provides a heterocyclic compound as a TYK2 pseudokinase (JH2) domain inhibitor, a synthetic method, and use. In particular, the present invention provides a heterocyclic compound as represented by formula I, or a pharmaceutically acceptable salt thereof, wherein groups are as defined in the text. The heterocyclic compound in the present invention has excellent TYK2 (JH2) selective inhibitory activity.

(I)

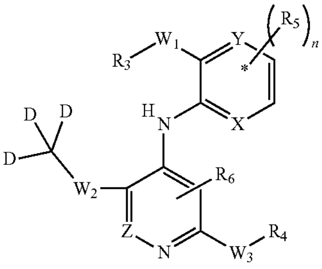

10 Claims, No Drawings

HETEROCYCLIC COMPOUND AS TYK2 PSEUDOKINASE DOMAIN INHIBITOR, SYNTHETIC METHOD, AND USE

TECHNICAL FIELD

The present invention belongs to the field of medicine, specifically, relates to a heterocyclic compound as TYK2 pseudokinase (JH2) domain inhibitor, synthetic method, and use

BACKGROUND

Janus kinase (JAK) is an intracellular non receptor tyrosine kinase that mediates the signal transduction and activation of various cytokines. The JAK kinase family is divided into four subtypes: JAK1, 2, 3, and TYK2. Each subtype mediates different types of cytokine signaling pathways. JAK1, 2, and TYK2 are expressed in various tissues and cells in the human body, while JAK3 is mainly expressed in hematopoietic tissue cells.

TYK2 is the earliest subtype discovered in the JAK family, mediating the function of cytokines such as IFN-α, IL-6, IL-10, IL-12, and IL-23. Studies have shown that TYK2 deletion mutation can effectively inhibit the occurrence of immune diseases such as allergies, autoimmune diseases, and inflammation. IL-23 plays a crucial role in the occurrence and development of psoriasis. Recent studies have shown that the pathogenesis of psoriasis is the secretion of IL-23 caused by the activation of antigen-presenting cells (APCs) by endogenous unknown antigen. IL-23 activates Thi7 cells to secrete cytokines such as IL-17, inducing keratinocyte differentiation and division and secretion of IL-23, further stimulating inflammation and keratinocyte proliferation to generate psoriasis. TYK2 and JAK2 jointly mediate the downstream signaling pathway of IL-23, while the inhibition of JAK2 may lead to anemia and other blood related side effects. Therefore, the inhibition of TYK2 while avoiding the inhibition of JAK2 is a good strategy for inhibiting the IL-23 signaling pathway. The first oral Tofacitinib belongs to non-selective JAK inhibitor, which has significant inhibitory activity on JAK1, 2, 3, and TYK2. It can selectively inhibit the catalytic domain (JH1 or "homology 1 domain of JAK protein") that binds to the adenosine triphosphate (ATP) site, preventing phosphorylation of downstream kinase catalytic activity and the resulting pathway signal transduction by blocking ATP. The inhibition of Tofacitinib on the activities of other subtypes such as JAK1, 2, 3, and TYK2 has increased its efficacy, but also brings about serious side effects, including infection, tuberculosis, tumors, anemia, liver damage, and increased cholesterol. Due to the correlation between JAK2 activity and red blood cell differentiation and lipid metabolism processes, some of above-mentioned side effects such as anemia are considered to be related to the insufficient selectivity of Tofacitinib towards JAK2, and are caused by the non-selective inhibition of the drug.

Given the excellent efficacy and serious side effects associated with multiple targets of JAK non-selective inhibitors, there is an urgent need for a TYK2 inhibitor in this field. Such inhibitor is functionally distinct from the binding catalytic domain (JH1) of previous JAK inhibitors, selectively binds to the TYK2 pseudokinase (JH2) domain, inhibits the function of the pseudokinase (JH2) domain, and avoids inhibiting other subtypes such as JAK1, 2, 3, and TYK2 (JH1), and increases the safety of TYK2 pseudokinase (JH2) inhibitor, thereby the inhibitor has enormous clinical potential in the treatment of various autoimmune and inflammatory related diseases associated with TYK2 pseudokinase (JH2) domain function, including psoriasis, lupus erythematosus, inflammatory bowel disease, psoriatic arthritis, arthritis, dermatitis, lupus nephritis, neuroinflammation such as multiple sclerosis and senile dementia, ankylosing spondylitis, hidradenitis suppurativa, respiratory disease, diabetes, inflammatory eye disease, hepatitis, cardiovascular disease, systemic sclerosis, organ transplantation, alopecia areata, acne, eczema, vitiligo, sjogren's syndrome, and certain cancers.

Therefore, there is an urgent need in this field to develop structurally novel TYK2 pseudokinase (JH2) domain inhibitors with high safety, and excellent efficacy.

SUMMARY OF THE INVENTION

The purpose of the present invention is to provide a structurally novel TYK2 pseudokinase (JH2) domain inhibitor with high safety and excellent efficacy.

In the first aspect of the present invention, provided is a heterocyclic compound or a pharmaceutically acceptable salt thereof, the compound is as shown in formula I (I)

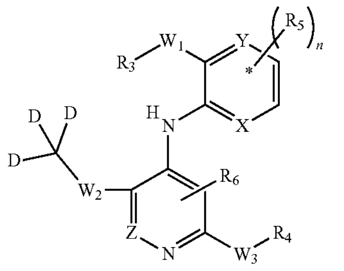

wherein,

X and Y are each independently $CR_5$ or N;

Z is $CR_6$ or N;

$W_1$ and $W_2$ are divalent group each independently selected from the group consisting of O, S, $SO_2$, CO, $NR_7CO$, and $CONR_7$;

$W_3$ is a divalent group selected from the group consisting of CO, $NR_7$, $NR_7CO$, $CONR_7$;

$R_3$ is substituted or unsubstituted $C_{3-6}$ cycloalkyl;

$R_4$ is selected from the group consisting of substituted or unsubstituted $C_{1-6}$ alkyl, substituted or unsubstituted $C_{3-6}$ cycloalkyl; and $R_4$ is optionally further substituted with $R_1$ and $R_2$;

$R_1$ and $R_2$ are each independently selected from the groups consisting of H, substituted or unsubstituted $C_{1-6}$ alkyl; or, $R_1$ and $R_2$ together with the carbon to which they are attached form a substituted or unsubstituted $C_{3-6}$ cycloalkyl;

$R_5$, $R_6$ and $R_7$ are each independently selected from the group consisting of H, substituted or unsubstituted $C_{1-4}$alkyl;

n=1 or 2;

unless otherwise specified, said substituted means that one or more hydrogen atoms in the group are substituted with substituents selected from the group consisting of halogen, $C_{1-4}$ alkyl, and $C_{1-4}$ haloalkyl.

In another preferred embodiment, $R_3$ is substituted or unsubstituted cyclopropyl.

In another preferred embodiment, $R_3$ is cyclopropyl.

In another preferred embodiment, X, Y, Z, $W_1$, $W_2$, $W_3$, $R_1$, $R_2$, $R_3$, $R_4$, $R_5$, $R_6$, $R_7$, and n are the corresponding groups in the specific compound (such as compounds shown in Table A, preferably compounds 2-5) in the example.

In another preferred embodiment the heterocyclic compound is as shown in formula IA;

(IA)

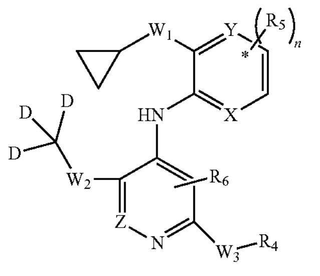

wherein, each group is defined as above.

In another preferred embodiment, the heterocyclic compound is as shown in formula IB;

(IB)

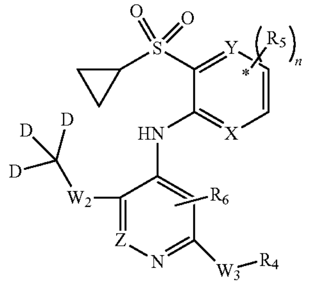

wherein, each group is defined as above.

In another preferred embodiment, the heterocyclic compound is as shown in formula IC;

(IC)

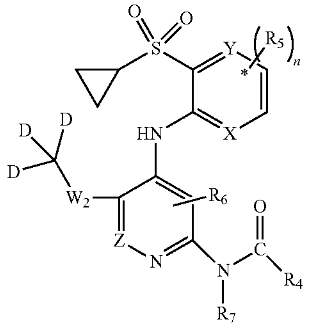

wherein, each group is defined as above.

In another preferred embodiment, the heterocyclic compound is shown in formula II;

(II)

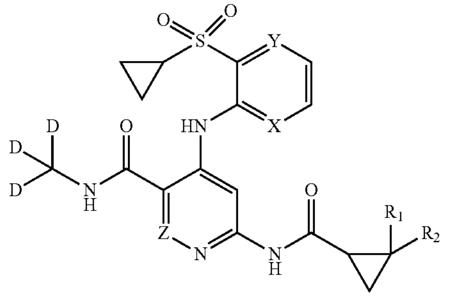

wherein,

X and Y are each independently $CR_5$ or N;

Z is $CR_6$ or N;

$R_1$ and $R_2$ are each independently selected from the group consisting of H, substituted or unsubstituted $C_{1-6}$ alkyl; or, $R_1$ and $R_2$ together with the carbon to which they are attached form substituted or unsubstituted $C_{3-6}$ cycloalkyl;

$R_5$ and $R_6$ are each independently selected from the group consisting of H, substituted or unsubstituted $C_{1-4}$ alkyl;

unless otherwise specified, said substituted means that one or more or hydrogen atoms in the group are substituted with substituent selected from the group consisting of halogen, $C_{1-4}$ alkyl, and $C_{1-4}$ haloalkyl;

In another preferred embodiment, $R_5$ and $R_6$ are both H.

In another preferred embodiment, X, Y and Z are each independently CH or N.

In another preferred embodiment, X is N.

In another preferred embodiment, Y is $CR_5$; preferably, Y is CH.

In another preferred embodiment, Z is N.

In another preferred embodiment, X and Z are N.

In another preferred embodiment, X is N, Y is $CR_5$ (preferably, X is N and Y is CH).

In another preferred embodiment, X is N, Y is $CR_5$ (preferably Y is CH), and Z is N.

In another preferred embodiment, $R_1$ and $R_2$ are H.

In another preferred embodiment, $R_1$ and $R_2$ together with the carbon to which they are attached form substituted or unsubstituted $C_{3-6}$ cycloalkyl.

In another preferred embodiment, $R_1$ and $R_2$ are H, or $R_1$ and $R_2$ together with the carbon to which they are attached form cyclopropyl.

In another preferred embodiment, X, Y, Z, $R_1$ and $R_2$ are the corresponding groups in the specific compound (such as compounds shown in Table A, preferably compounds 2-5) in the example.

In another preferred embodiment, the compound is a compound selected from Table A:

TABLE A

Compound 1

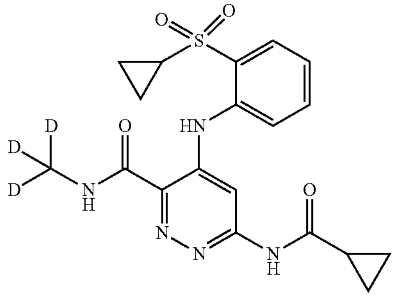 [SMILES: [2H]C([2H])([2H])NC(=O)c1nnc(NC(=O)C2CC2)cc1Nc1ccccc1S(=O)(=O)C1CC1]

TABLE A-continued
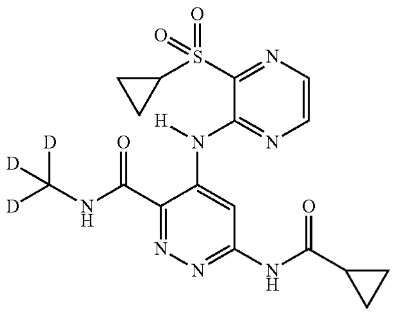 [SMILES: [2H]C([2H])([2H])NC(=O)c1nnc(NC(=O)C2CC2)cc1Nc1nccnc1S(=O)(=O)C1CC1]
Compound 2
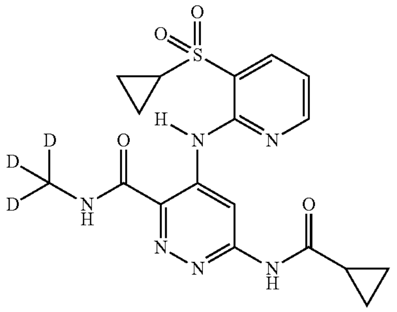 [SMILES: [2H]C([2H])([2H])NC(=O)c1nnc(NC(=O)C2CC2)cc1Nc1ncccc1S(=O)(=O)C1CC1]
Compound 3
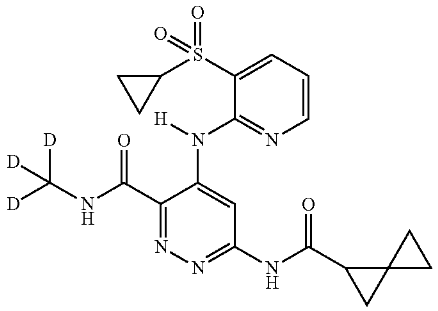 [SMILES: [2H]C([2H])([2H])NC(=O)c1nnc(NC(=O)C2CC23CC3)cc1Nc1ncccc1S(=O)(=O)C1CC1]
Compound 4
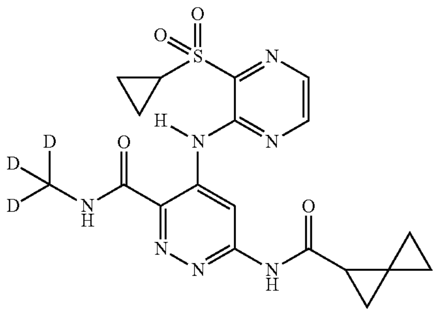 [SMILES: [2H]C([2H])([2H])NC(=O)c1nnc(NC(=O)C2CC23CC3)cc1Nc1nccnc1S(=O)(=O)C1CC1]
Compound 5
TABLE A-continued
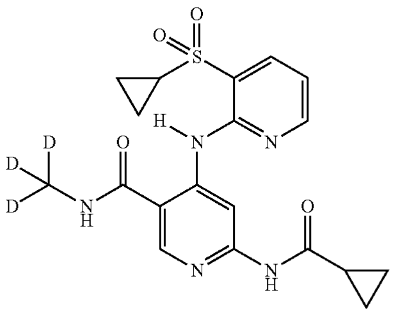 [SMILES: [2H]C([2H])([2H])NC(=O)c1cnc(NC(=O)C2CC2)cc1Nc1ncccc1S(=O)(=O)C1CC1]
Compound 6
In the second aspect of the present invention, provided is an intermediate for preparing the heterocyclic compound according to the first aspect, the intermediate is as shown in formula III, formula IIIA, formula IIIB, formula IIIC or formula IV:
(III)
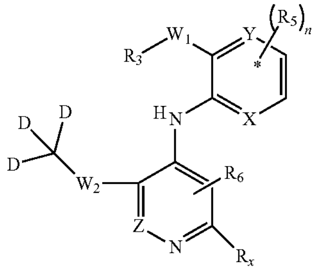
(IIIA)
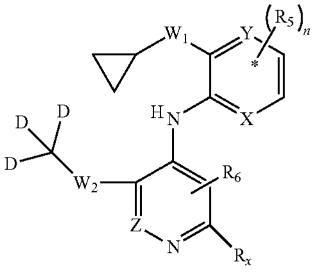
(IIIB)
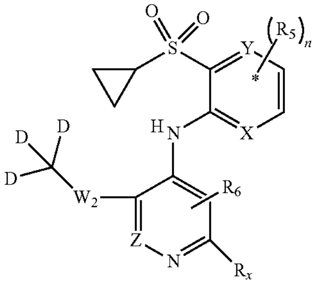

-continued (IV)

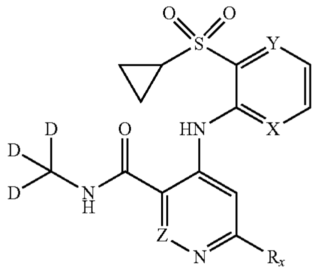

wherein, $R_X$ is halogen; X, Y, Z, $W_1$, $W_2$, $W_3$, $R_1$, $R_2$, $R_3$, $R_4$, $R_5$, $R_6$, $R_7$, and n are as defined in the first aspect.

In another preferred embodiment, $R_X$ is Cl.

In the third aspect of the present invention, provided is a preparation method of the heterocyclic compound according to the first aspect, wherein, the heterocyclic compound is shown in formula I, and wherein $W_3$ is $NR_7CO$; the method comprises the steps of:

reacting the intermediate of formula III with the compound of formula V, thereby obtaining the compound of formula I;

(V)

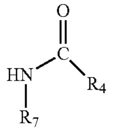

wherein, $R_4$ and $R_7$ are as defined in the first aspect.

In another preferred embodiment, reacting the intermediate of formula IV with the compound of formula VI, thereby obtaining the compound of formula II (VI)

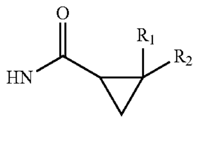

wherein, $R_1$ and $R_2$ are as defined in the first aspect.

In the fourth aspect of the present invention, provided is a pharmaceutical composition, comprising (i) the heterocyclic compound according to the first aspect or pharmaceutically acceptable salts thereof, and (ii) pharmaceutically acceptable carriers or excipients.

In the fifth aspect of the present invention, provided is a use of the heterocyclic compound according to the first aspect in the preparation of (i) drugs for treating or preventing TYK2 mediated diseases and/or (ii) TYK2 inhibitors.

In another preferred embodiment, the TYK2 mediated disease is IL-23, IL-12, and/or IFN α related diseases.

In another preferred embodiment, the heterocyclic compound treat or prevent TYK2-JH2 mediated diseases by electively inhibiting TYK2-JH2.

In another preferred embodiment, the TYK2-JH2 mediated diseases include inflammation, autoimmune diseases, or combinations thereof.

In another preferred embodiment, the TYK2-JH2 mediated diseases comprise psoriasis, lupus erythematosus, inflammatory bowel disease, psoriatic arthritis, arthritis, dermatitis, lupus nephritis, neurogenic inflammation such as multiple sclerosis and senile dementia, ankylosing spondylitis, hidradenitis suppurativa, respiratory disease, diabetes, inflammatory eye disease, hepatitis, cardiovascular disease, systemic sclerosis, organ transplantation, alopecia areata, acne, eczema, vitiligo, sjogren's syndrome, cancer or combinations thereof.

In another preferred embodiment, the TYK2-JH2 inhibitor is a selective TYK2-JH2 inhibitor.

In the sixth aspect of the present application, provided is a method of selectively inhibiting TYK2, comprising:

contacting the subject with the heterocyclic compound according to the first aspect, thereby inhibiting the activity of TYK2-JH2 in the subject.

In another preferred embodiment, the subject is a cell or TYK2 Kinase.

In another preferred embodiment, the inhibition is selective inhibition on TYK2-JH2.

In another preferred embodiment, the method is in vitro and non-therapeutic.

In the seventh aspect of the present invention, provided is a method of treating or preventing TYK2 mediated diseases, comprising the steps of administering a safe and effective amount of the heterocyclic compound according to the first aspect or the pharmaceutical composition according to the third aspect to a human in need thereof, thereby inhibiting or In another preferred embodiment, the TYK2 mediated disease is IL-23, IL-12, and/or IFN α related diseases.

In another preferred embodiment, the heterocyclic compound treat or prevent TYK2-JH2 mediated diseases by electively inhibiting TYK2-JH2.

In another preferred embodiment, the TYK2-JH2 mediated diseases include inflammation, autoimmune diseases, or combinations thereof.

In another preferred embodiment, the TYK2-JH2 mediated diseases comprise psoriasis, lupus erythematosus, inflammatory bowel disease, psoriatic arthritis, arthritis, dermatitis, lupus nephritis, neurogenic inflammation such as multiple sclerosis and senile dementia, ankylosing spondylitis, hidradenitis suppurativa, respiratory disease, diabetes, inflammatory eye disease, hepatitis, cardiovascular disease, systemic sclerosis, organ transplantation, alopecia areata, acne, eczema, vitiligo, sjogren's syndrome, cancer or combinations thereof.

It should be understood that within the scope of the present invention, the above technical features of the present invention and the technical features specifically described in the following (e.g., embodiments) can be combined with each other, thereby forming a new or preferred technical solution. Due to space limitations, it will not be repeated herein.

EMBODIMENTS FOR CARRYING OUT THE INVENTION

After extensive and in-depth research, the inventor found that the compound having novel structure of the present invention has excellent selective inhibition on TYK2 (JH2), and thus the present invention provides a compound with higher safety that can effectively suppress the desired target without affecting other un-desired targets. Based on this, the inventor completed the present invention.

Terms

As used herein, the term "halogen" refers to F, Cl, Br or I. Correspondingly, "halo" means one or more hydrogen in the group is substituted with F, Cl, Br, or I.

Unless otherwise stated, the term “alkyl”, by itself or as part of another substituent, means, a straight or branched chain hydrocarbon radical, having a designated number of carbon atoms (i.e. $C_{1-6}$ means 1 to 6 carbons). Examples of alkyl include methyl, ethyl, n-propyl, isopropyl, n-butyl, t-butyl, iso-butyl, sec-butyl, n-pentyl, n-hexyl, and the like.

The term “alkenyl” refers to an unsaturated alkyl group having one or more double bonds. Preferably, the alkenyl comprises 1 to 4 carbons, i.e., $C_{1-4}$ alkenyl. Similarly, the term “alkynyl” refers to an unsaturated alkyl group having one or more triple bonds (preferably, having one triple bond). Preferably, the alkenyl comprises 1 to 4 carbons. Examples of these unsaturated alkyl groups include vinyl, 2-propenyl, ethynyl, 1- and 3-propynyl, 3-butynyl, and so on.

The term “cycloalkyl” refers to a hydrocarbon ring with a specified number of ring atoms (for example, $C_{3-6}$ cycloalkyl has 3-6 ring atoms) and is completely saturated. “Cycloalkyl” is also meant to refer to bicyclic and polycyclic hydrocarbon rings such as, bicyclo[2.2.1]heptane, bicyclo[2.2.2]octane, etc.

The term “alkylene” by itself or as a part of another substituent means a divalent radical derived from an alkane, as exemplified by $—CH_2—$ or $—CH_2CH_2CH_2—$. Alkyl (or alkylene) typically has 1-4 carbon atoms. Similarly, “alkenylene” and “alkynylene” refer to the unsaturated forms of “alkylene” having a double or triple bond, respectively Substituents for the alkyl radicals (including those groups often referred to as alkylene, alkenyl, alkynyl and cycloalkyl) can be a variety of groups selected from the group consisting of -halogen, —OR', —NR'R", —SR', —OC(O)R', —C(O)R', $—CO_2R'$, —CONR'R", —OC(O)NR'R", —NR"C(O)R', —NR'—C(O)NR"R", $—NR"C(O)_2R'$, $—NH—C(NH_2)═NH$, $—NR'C(NH_2)═NH$, $—NH—C(NH_2)═NR'$, —S(O)R', $—S(O)_2R'$, $—S(O)_2NR'R"$, $—NR'S(O)_2R"$, —CN and $—NO_2$ in a number ranging from zero to (2m'+1), wherein, m' is the total number of carbon atoms in such radical. R', R" and R"' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy, or unsubstituted aryl-$C_{1-4}$ alkyl groups. When R' and R" are attached to the same nitrogen atom, they can combined with the nitrogen atom to form a 3-, 4-, 5-, 6-, or 7-membered ring. For example, —NR'R" is meant to include 1-pyrrolidinyl and 4-morpholinyl. The term “acyl” as used by itself or as part of another group, refers to groups wherein two substitutents on the carbon that is closest to the point of attachment for the radical is replaced with the substitutent ═O (e.g., $C(O)CH_3$, $—C(O)CH_2CH_2OR'$ and the like).

As used herein, the term “heteroatom” is meant to include oxygen (O), nitrogen (N), sulfur (S) and silicon (Si); preferably, heteroatom includes oxygen (O), nitrogen (N), sulfur (S).

For the compounds provided herein, a bond that is drawn from a substituent (typically an R group) to the center of an aromatic ring (e.g., benzene, pyridine, and the like) will be understood to refer to a bond providing a connection at any of the available vertices of the aromatic ring. In some embodiments, the depiction will also include connection at a ring which is fused to the aromatic ring. For example, a bond drawn to the center of the benzene portion of an indole, will indicate a bond to any available vertex of the six- or five-membered ring portions of the indole.

As used herein, the term “containing”, “comprising” or “including” means that the various components can be used together in the mixture or composition of the present invention. Therefore, the terms “mainly consisting of . . . ” and “consisting of . . . ” are within the term “comprising”.

As used herein, the term “pharmaceutically acceptable” component(s) refer to a substance suitable for use in human and/or animals without excessive adverse side reactions (such as toxicity, stimulation and allergic reaction), i.e. a substance with reasonable benefit/risk ratio.

Unless otherwise specified, all compounds present in the present invention are intended to include all possible optical isomers, such as single chiral compounds or mixtures of various chiral compounds (i.e. racemes). Among all compounds of the present invention, each chiral carbon atom may optionally be of the R or S configuration, or a mixture of the R and S configurations.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure. When the compounds herein have an identified stereochemistry (indicated as R or S, or with dash or wedge bond designations), those compounds will be understood by one of skill in the art to be substantially free of other isomers (e.g., at least 80%, 90%, 95%, 98%, 99%, and up to 100% free of the other isomer).

The compounds of the present disclosure may also contain unnatural proportions of atomic isotopes at one or more of isotopic atoms that constitute such compounds. The unnatural proportions of certain isotope can be defined as the amount from the naturally found amount of the atom of interest to 100% of that atom. For example, the compounds may incorporate radioactive isotopes, such as tritium ($^3H$), iodine-125 ($^{125}I$) or carbon-14 ($^{14}C$), or non-radioactive isotopes, such as deuterium ($^2H$) or carbon-13 ($^{13}C$). Such isotopic variants may provide additional uses in addition to those described in this application. For instance, isotopic variants of the compounds of the disclosure may have additional uses, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics, contributing to enhanced safety, tolerability or efficacy during treatment. All isotopic variants of the compounds of the present disclosure, whether radioactive or not, should be encompassed within the scope of the present disclosure.

Active Ingredients

As used herein, the term “compound of the invention” or “heterocyclic compound of the invention” refers to the compound of formula (I) or (II). This term also includes various crystalline forms, pharmaceutically acceptable salts, hydrates or solvates of the compound of formula (I) or (II).

Wherein, the term “pharmaceutically acceptable salts” refers to salts that formed of the compound of the invention and acids or bases, and suitable for use as a drug. Pharmaceutically acceptable salts include inorganic salts and organic salts. A group of preferred salts are salts formed of the compound of the present invention and acids. Acids suitable for forming salts include, but are not limited to, inorganic acids such as hydrochloric acid, hydrobromic acid, hydrofluoric acid, sulfuric acid, nitric acid, phosphoric acid and the like; organic acids such as methanoic acid, acetic acid, trifluoroacetic acid, propionic acid, oxalic acid, malonic acid, succinic acid, fumanic acid, maleic acid, lactic acid, malic acid, tartaric acid, citric acid, bitter acid, benzoic acid, methanesulfonic acid, ethanesulfonic acid, p-toluenesulfonic acid, benzenesulfonic acid, naphthalene sulfonic acid, and the like; and amino acids such as proline, phenylalanine, aspartic acid, glutamic acid and the like. Another preferred type of salts are salts formed by compounds of the present invention and bases, e.g., alkali metal salts (e.g. sodium or potassium salts), alkaline earth metal salts (e.g. calcium or magnesium salts), ammonium salts (e.g., lower alkanol ammonium salts or other pharmaceutically acceptable amine salts), for example, methylamine salt, ethylamine salt, propylamine salt, dimethylamine salt, trimethylamine salts, diethylamine salts, triethylamine salts, tert-butyl amine salts, ethylenediamine salts, hydroxyethylamine salts, bi-hydroxyethylamine salts, tri-hydroxyethylamine salts, and amine salts formed by morpholine, piperazine, and lysine, respectively.

The term "solvate" refers to complexes formed of the compound of the present invention and solvent molecules in any specific ratio. The "hydrate" refers to complexes formed of the compound of the present invention and water.

Moreover, the compound of the present invention further comprises prodrugs of the heterocyclic compound of formula (I) or (II). The term "prodrug", including itself, is biologically active or non-active, when being administered in a suitable way, the prodrugs undergo metabolism or chemical reaction in the human body and converted to a class of compound of formula (I) or a salt or solutions containing compound of formula (I). The prodrugs include (but are not limited to) the carboxylic acid ester, carbonic ester, phosphate, nitrate, sulfate, sulfone ester, sulfoxide esters, amino compounds, carbamates, azo compounds, phosphoramides, glucoside, ether, acetal form of the compound, etc.

Preparation Method

The following provides a more specific description of the preparation methods for the compounds having a structure of formula (I) or formula (II) of the present invention, but these specific methods do not pose any limitations to the present invention. The compound of the present invention can also be conveniently prepared by combining various synthesis methods described in this specification or known in the art, and such combinations can be easily carried out by those skilled in this field to which the present invention belongs.

Pharmaceutical Compositions and Administration Method

Because the compounds of the invention have excellent selective inhibitory activity against TYK2 pseudokinase (JH2) domain, the compounds of the invention and various crystal forms, pharmaceutically acceptable inorganic or organic salts, hydrates or solvates thereof, and pharmaceutical compositions containing the compounds of the present invention as active ingredient can be used in the treatment, prevention and alleviation of diseases mediated by TYK2 kinase. According to the prior art, the compounds of the invention can be used to treat the following diseases: psoriasis, lupus erythematosus, inflammatory bowel disease, psoriatic arthritis, arthritis, dermatitis, lupus nephritis, neurogenic Inflammation such as multiple sclerosis and senile dementia, ankylosing spondylitis, hidradenitis suppurativa, respiratory disease, diabetes, inflammatory eye disease, hepatitis, cardiovascular disease, systemic sclerosis, organ transplantation, alopecia areata, acne, eczema, vitiligo, sjogren's syndrome, and some cancers and other autoimmune and inflammatory related diseases.

As used herein, the term "selective" refers to the activity or potency (such as inhibitory activity) against a specified target (such as TYK2 (JH2)) being higher than the activity or potency (inhibitory activity) against other targets (such as JAK1, 2, 3 (JH1 and JH2), and/or TYK2 (JH1)); for example, the activity or potency (such as inhibitory activity) against a specified target (such as TYK2 (JH2)) being at least 50 times of the activity or potency (such as inhibitory activity) against other targets (such as JAK1, 2, 3 (JH1 and JH2), and/or TYK2 (JH1)). For example, when the IC50 value is used to quantify the inhibitory activity, $IC50_{Other}/IC50_{TYK2\text{-}JH2}>50$, wherein, $IC50_{TYK2\text{-}JH2}$ refers to the inhibitory activity IC50 (nM) of the heterocyclic compound against TYK2-JH2 (a pseudokinase domain of TYK2), and $IC50_{Other}$ refers to the inhibitory activity IC50 (nM) of the heterocyclic compound against one or more of the following kinases: TYK2-JH1 (the kinase domain of TYK2), JAK1-JH1 (the kinase domain of JAK1), JAK1-JH2 (pseudokinase domain of JAK1), JAK2-JH1 (the kinase domain of JAK2), and JAK3-JH1 (the kinase domain of JAK3).

The pharmaceutical composition of the invention comprises the compound of the present invention or the pharmaceutically acceptable salts thereof in a safe and effective dosage range, and pharmaceutically acceptable excipients or carriers. Wherein "Safe and effective amount" refers to that the amount of compound is sufficiently enough to significantly improve the condition, without generating severe side effects. Generally, the pharmaceutical composition contains 1-200 mg of compounds of the invention per dose, preferably, 1-50 mg of compounds of the invention per dose. Preferably, the "one dose" is one capsule or one pill.

"Pharmaceutically acceptable carrier" means one or more compatible solid or liquid fillers, or gelatinous materials which are suitable for human use and should be of sufficient purity and with sufficiently low toxicity. "Compatibility" used herein means that the components of the composition can be admixed with the compounds of the invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compound or pharmaceutical compositions of the present invention, and the representative administration mode includes (but is not limited to): oral, intratumoral, rectal, parenteral (intravenous, intramuscular or subcutaneous), and topical administration. Solid dosage forms for oral administration include capsules, tablets, pills, powders and granules. In these solid dosage forms, the active compounds are mixed with at least one conventional inert excipient (or carrier), such as sodium citrate or $Ca_2HPO_4$, or mixed with the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or mixtures thereof. In capsules, tablets, and pills, the dosage form may also include buffer.

Solid dosage forms such as tablets, sugar pills, capsules, pills, and granules can be prepared using coating and shell materials, such as casings and other well-known materials in the art. They can contain an opaque agent. The release of the active compound or compounds in the compositions can be released in a delayed fashion in a given part of the digestive tract. Examples of embedding components that can be used are polymeric substances and waxes. If necessary, the active compound can also form microcapsules with one or more of the aforementioned excipients.

Liquid dosage forms for oral administration include pharmaceutically acceptable emulsions, solutions, suspensions, syrups or tinctures. In addition to active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or combinations thereof.

In addition to these inert diluents, the composition can also include additives such as wetting agents, emulsifiers and suspending agents, sweeteners, corrigents, and spices.

In addition to active compounds, suspensions can include suspending agents such as ethoxylated isooctadecanol, polyoxyethylene sorbitol and dehydrated sorbitol esters, microcrystalline cellulose, methanol aluminum and agar, or mixtures of these substances.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols, and their suitable mixtures.

The dosage forms of the compound of the present invention used for topical administration include ointments, powders, patches, sprays, and inhalants. The active ingredients are mixed under sterile conditions with physiologically acceptable carriers and any preservatives, buffers, or propellantsif necessary.

The compound of the present invention can be administered separately or in combination with other pharmaceutically acceptable compounds.

When the pharmaceutical compositions are used, a safe and effective amount of compound of the present invention is applied to a mammal (such as human) in need thereof, wherein the dose of administration is a pharmaceutically effective dose. For a person weighed 60 kg, the daily dose is usually 1-200 mg, preferably 1-50 mg. Of course, the specific dosage should also consider factors such as the route of administration and the patient's health status, which are within the skill range of a skilled physician.

The main advantages of the present invention include:

1. The compound of the present invention has excellent selectivity. Compared with JH1 and JH2 of JAK1, 2, and 3 as well as JH1 of TYK2, the compounds of the present invention have better inhibitory activity against JH2 of TYK2. Therefore, the compounds of the present invention are less likely to act on other similar kinases and have superior safety.
2. The compound of the present invention has excellent selectivity and inhibitory activity.

The present invention was further described hereafter in combination with specific embodiments. It should be understood that these examples are only used to illustrate the present invention and not to limit the scope of the invention. The experimental methods with no specific conditions described in the following examples are generally performed under the conventional conditions, for example, according to J. Sambrook et al., Molecular Cloning: A Laboratory Manual, 3rd Edition, Science Press, 1989, or according to the manufacture's instructions. Unless otherwise stated, percentages and parts are percentages by weight and parts by weight.

PREPARATION EXAMPLE

Example 1

Synthesis of Compound 1

Compound 1

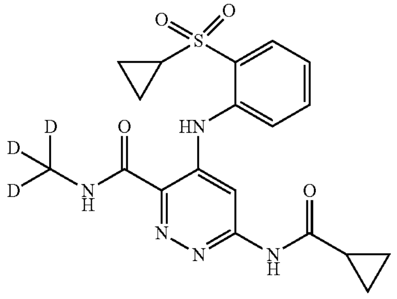 [SMILES: [2H]C([2H])([2H])NC(=O)c1nnc(NC(=O)C2CC2)cc1Nc1ccccc1S(=O)(=O)C1CC1]

Step A

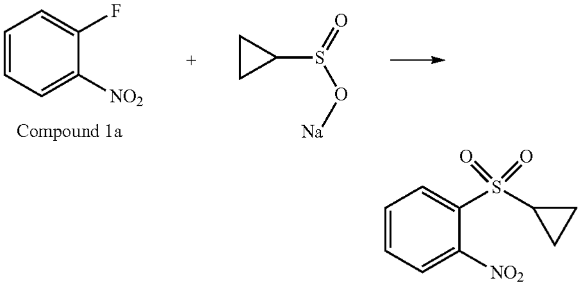

Compound 1a

Compound 1b

Compound 1a (6.4 g, 0.045 mol, 1.0 eq), dimethyl sulfoxide (100 ml), sodium cyclopropanesulfinate (6.4 g, 0.06 mol, 1.2 eq) were added to a 250 ml three-necked flask under the protection of nitrogen. The mixture was heated and stirred at 100° C. to react for 1 hour.

The reaction was detected by TLC until complete, and then cooled down. The reaction solution was poured into ice water (600 ml), and extracted 3 times with methyl tert-butyl ether. The combined organic phase was washed twice with saturated salt water, dried with $Na_2SO_4$, concentrated, and underwent beating with petroleum ether, to obtain solid compound 1b as white powder (7.8 g, 0.034 mol, yield 76%). 1H NMR (300 MHz, CDC13): 8.05 (m, 1H), 7.7-7.9 (m, 3H), 3.2-3.3 (m, 1H), 1.3-1.5 (m, 2H), 1.0-1.2 (m, 2H).

Step B

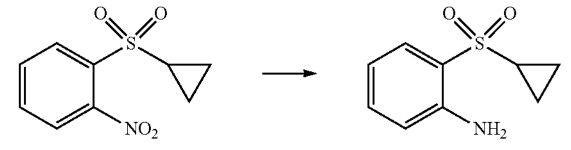

Compound 1b Compound 1c

Compound 1b (3.2 g, 0.014 mol, 1.0 eq), ethanol (100 ml), and Pd/C (10%, 1.0 g) were added into a 250 mL single-neck flask at room temperature. The hydrogenation reaction was conducted using hydrogen bag for 3 hours. TLC showed that the raw materials were completely reacted. The reaction was filtrated, concentrated and separated by column chromatography to obtain compound 1c as white solid (2.6 g, 0.013 mol, yield 94%). 1H NMR (300 MHz, CDC13): 7.65 (m, 1H), 7.2-7.4 (m, 1H), 6.7-6.9 (m, 2H), 2.6-2.8 (m, 1H), 1.3-1.4 (m, 2H), 0.9-1.0 (m, 2H).

Step C

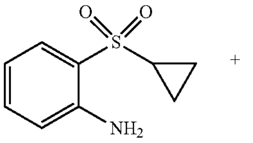

Compound 1c

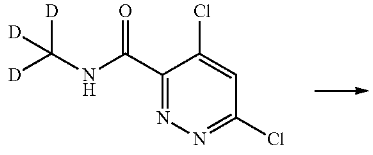

Compound 1d

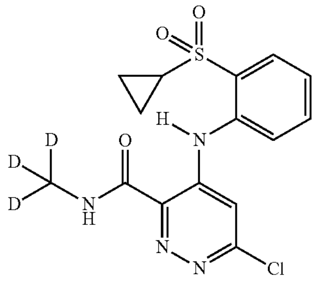

Compound 1f

Compound 1c (0.8 g, 4 mmol, 1.0 eq), compound 1d (0.91 g, 4.4 mmol, 1.1 eq), and THF (40 ml) were added under nitrogen protection to a 100 ml three necked flask. NaHMDS (2M, 3 ml, 6 mmol) was added dropwise at 0-5° C. After completion, the mixture was reacted at room temperature for 1 hour. TLC showed that the raw materials were completely reacted. The reaction solution was poured into a cold saturated ammonium chloride aqueous solution (200 ml), extracted twice with ethyl acetate. The combined organic phase was washed twice with saturated salt water, dried with $Na_2SO_4$, concentrated, and separated by column chromatography to obtain compound if as light yellow solid (0.4 g, 1 mmol, yield 94%). MS-ESI: [M+1]+=370.9. 1H NMR (300 MHz, CDC13): 11.4 (s, 1H), 8.2 (s, 1H), 8.0 (m, 1H), 7.7 (m, 1H), 7.4-7.6 (m, 2H), 7.1 (s, 1H), 2.5-2.7 (m, 1H), 1.2-1.4 (m, 2H), 0.97-1.04 (m, 2H).

Step D

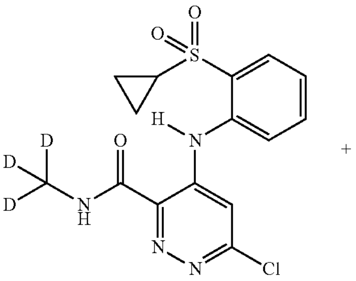

Compound 1f

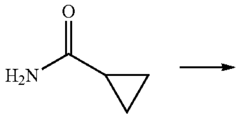

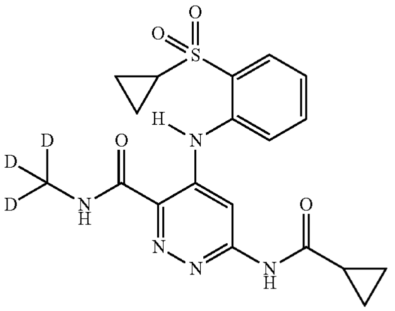

Compound 1

Compound if (0.4 g, 1.0 mmol, 1.0 eq), 1,4-dioxane (30 ml), cyclopropylformamide (0.14 g, 1.63 mol, 1.5 eq), $Pd_2(dba)_3$ (0.1 g), DPPF (0.01 g), and 2M $K_3PO_4$ aqueous solution (1.6 ml, 3.24 mol, 3.0 eq) were added into a 100 mL single-neck flask under nitrogen protection. The mixture was reacted overnight at 110° C. TLC showed that the raw materials were not fully reacted. The reaction was concentrated, speratated by column chromatography to obtain compound 1 as yellow powder (90 mg, 0.22 mmol, yield 22%).

MS-ESI: [M+1]+=419.5. 1H NMR (300 MHz, d6-DMSO): 11.35 (s, 1H), 11.06 (s, 1H), 9.09 (s, 1H), 8.04 (s, 1H), 7.89 (m, 1H), 7.7-7.73 (m, 2H), 7.42 (m, 1H), 2.75 (m, 1H), 2.03 (m, 1H), 0.75-1.02 (m, 8H).

Example 2

Synthesis of Compound 2

Compound 2

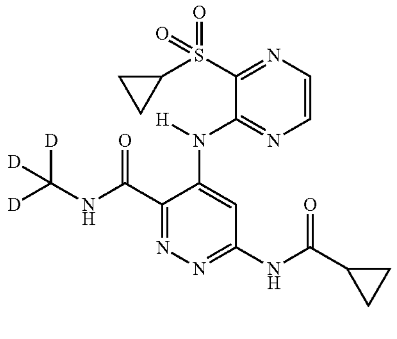 [SMILES: [2H]C([2H])([2H])NC(=O)c1nnc(NC(=O)C2CC2)cc1Nc1nccnc1S(=O)(=O)C1CC1]

Step A

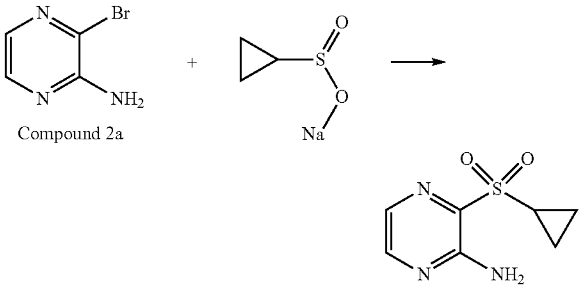

Compound 2a

Compound 2b

Compound 2a (10 g, 0.0575 mol, 1.0 eq), dimethyl sulfoxide (100 ml), sodium cyclopropanesulfinate (11 g, 0.086 mol, 1.5 eq), L-proline (1.32 g, 0.2 eq), cuprous iodide (1.1 g, 0.1 eq), and sodium hydroxide (0.46 g, 0.2 eq) were added under nitrogen protection to a 250 mL three necked flask. The mixture was reacted at 150° C. for 48 hours. TLC showed that the raw materials were completely reacted. The mixture was cooled down, poured into ice water (2 L), and extracted twice with ethyl acetate. The combined organic phase was washed twice with saturated salt water, dried, concentrated, and separated by column chromatography to obtain compound 2b as white powder (6.6 g, 0.0331 mol, yield 57.6%). MS-ESI: [M+1]+=200.2. 1H NMR (300 MHz, CDCl3): 8.24 (d, 1H), 8.01 (d, 1H), 2.8-2.9 (m, 1H), 1.4-1.5 (m, 2H), 1.05-1.15 (m, 2H).

Step B

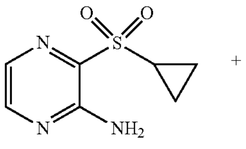

Compound 2b

-continued

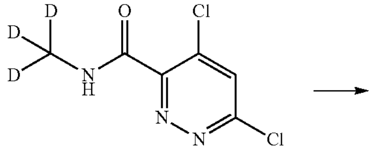

Compound 1d

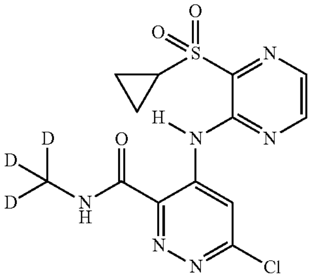

Compound 2c

Compound 2b (0.4 g, 2 mmol, 1.0 eq) and THF (20 ml) were added to a 100 ml three-necked flask under nitrogen protection. NaHMDS (2M, 1.5 ml, 3 mmol) was added dropwise at 0-5° C. The mixture was stirred at room temperature for 30 mins before compound 1d (0.42 g, 2 mmol, 1.0 eq) was added. TLC detection showed that the raw materials were not fully reacted. Even if the reaction time was extended, the reaction remains unchanged. The reaction was poured into ice water, extracted with ethyl acetate, washed with saturated salt water, dried, concentrated, and separated by column chromatography to obtain compound 2c as white powder (0.53 g, 1.42 mmol, yield 71%). MS-ESI: [M+1]+=372.8.

Step C

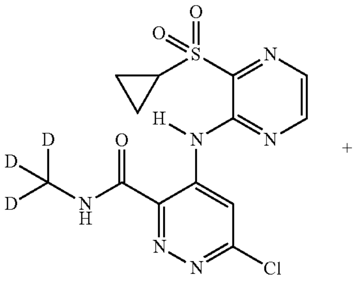

Compound 2c

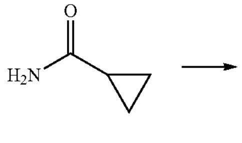

-continued

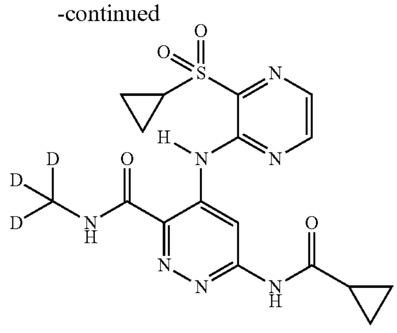

Compound 2

Compound 2c (0.25 g, 0.67 mmol, 1.0 eq), dioxane (20 ml), cyclopropylformamide (85 mg, lmmol, 1.5 eq), $Pd_2(dba)_3$ (50 mg), and DPPF (60 mg) were added into a 100 mL single-neck flask and the reaction was replaced with nitrogen for 3 times. The mixture was stirred for 5 min, then added with $K_3PO_4$ aqueous solution (1 ml, 2M, 3.0 eq), and replaced with nitrogen for 3 times. The mixture was reacted overnight at 112° C. TLC showed that the raw materials were not fully reacted. The reaction was concentrated, separated by column chromatography and then underwent beating with methyl tert-butyl ether to obtain compound 2 as yellow powder (80 mg, 0.19 mmol, yield 28.5%). MS-ESI: [M+1]+=421.5. 1H NMR (300 MHz, d6-DMSO): 12.3 (s, 1H), 11.5 (s, 1H), 9.44 (s, 1H), 9.18 (s, 1H), 8.67 (d, 1H), 8.44 (d, 1H), 3.16 (m, 1H), 2.13 (m, 1H), 1.10-1.22 (m, 4H), 0.86-0.88 (m, 4H).

Example 3

Synthesis of Compound 3

Compound 3

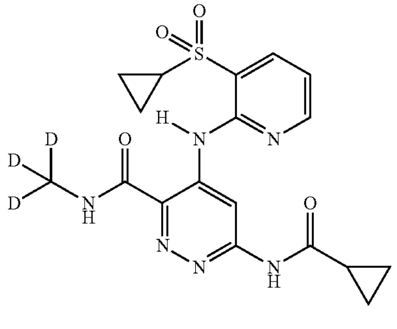

Step A

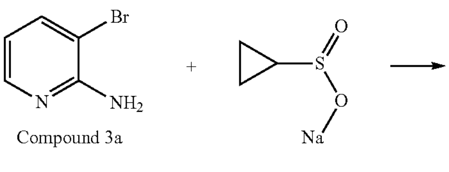

Compound 3a

-continued

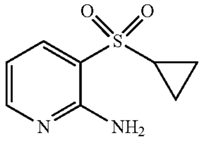

Compound 3b

Compound 3a (25 g, 0.144 mol, 1.0 eq), dimethyl sulfoxide (300 ml), sodium cyclopropanesulfinate (28 g, 0.218 mol, 1.5 eq), L-proline (3.3 g, 0.2 eq), cuprous iodide (2.74 g, 0.1 eq), and sodium hydroxide (1.2 g, 0.2 eq) were added under nitrogen protection to a 500 mL three-necked flask. The mixture was reacted at 150° C. for 48 hrs. TLC showed that the raw materials were completely reacted. The mixture was cooled down, poured into ice water (2 L), and extracted twice with ethyl acetate. The combined organic phase was washed twice with saturated salt water, dried over $Na_2SO_4$, concentrated, and underwent beating with petroleum ether-methyl tert-butyl ether to obtain compound 3b as beige powder (16 g, 0.081 mol, yield 56.1%). MS-ESI: [M+1]+=199.2. 1H NMR (300 MHz, CDCl3): 8.25-8.27 (d, 1H), 7.87-7.90 (m, 1H), 6.73-6.78 (m, 1H), 2.60-2.70 (m, 1H), 1.29-1.35 (m, 2H), 0.97-1.05 (m, 2H).

Step B

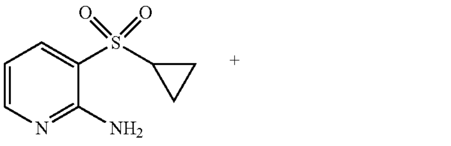

Compound 3b

Compound 1d

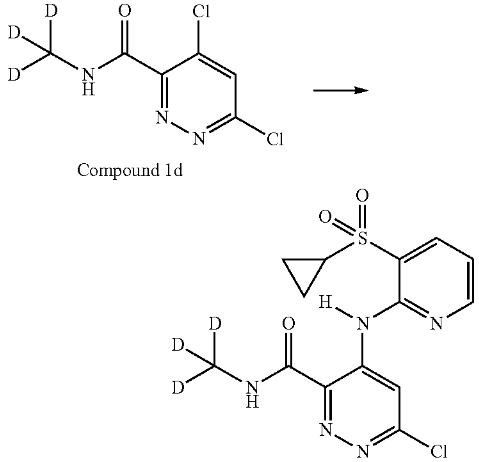

Compound 3c

Compound 3b (5.5 g, 0.028 mol, 1.0 eq) and THF (200 ml) were added to a 500 ml three-necked flask under nitrogen protection. NaHMDS (2M, 21 ml, 0.042 mol, 1.5 eq) was added dropwise at 0-5° C. The mixture was stirred at room temperature for 30 mins. Compound 1d (6.3 g, 0.03 mol, 1.1 eq) was further added under ice bath. The mixture was stirred at room temperature for 1 hr. TLC showed that the raw materials were completely reacted. The reaction was poured into a cold saturated ammonium chloride aqueous solution (100 ml), and the mixture was added with methyl tert-butyl ether (100 ml), and stirred for 10 min to precipitate solid. The mixture was filtered, washed with water, washed with ethyl acetate and dried to obtain compound 3c as white powder (3.1 g, 8.3 mmol, yield 30%). MS-ESI: [M+1]+=371.9. 1H NMR (300 MHz, d6-DMSO): 12.3 (s, 1H), 9.40 (s, 1H), 8.88 (s, 1H), 8.70 (d, 1H), 8.25-8.28 (m, 1H), 8.37-8.41 (m, 1H), 3.12 (m, 1H), 1.18 (m, 2H), 1.09 (m, 2H).

Step C

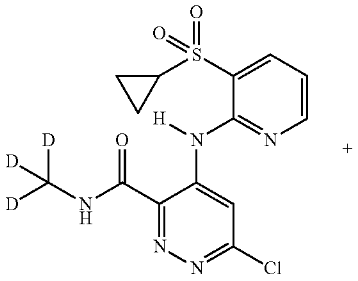

Compound 3c

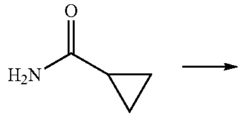

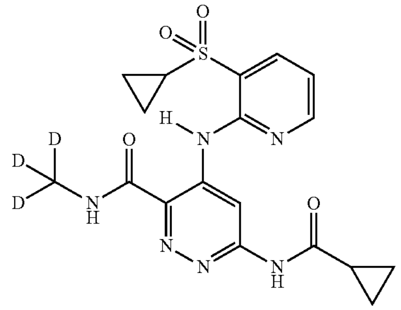 [SMILES: [2H]C([2H])([2H])NC(=O)c1nnc(NC(=O)C2CC2)cc1Nc1ncccc1S(=O)(=O)C1CC1]

Compound 3

Compound 3c (3.1 g, 8.3 mmol, 1.0 eq), dioxane (150 ml), cyclopropylformamide (1.1 g, 13.0 mmol, 1.6 eq), $Pd_2(dba)_3$ (0.5 g), and DPPF (0.6 g) were added into a 250 mL single-neck flask and replaced with nitrogen for 3 times. The mixture was stirred for 5 min, then added with $K_3PO_4$ aqueous solution (12.5 ml, 2M, 3.0 eq), and replaced with nitrogen for 3 times.

The mixture was reacted overnight at 112° C. TLC showed that the raw materials were not fully reacted. The reaction was concentrated, and separated by column chromatography to obtain compound 3 as white powder (1.25 g, 3 mmol, yield 36%). MS-ESI: [M+1]+=420.5. 1H NMR (300 MHz, CDCl3): 12.4 (s, 1H), 9.66 (s, 1H), 9.23 (s, 1H), 8.62 (m, 1H), 8.16-8.23 (m, 2H), 7.12-7.16 (m, 1H), 2.82-2.90 (m, 1H), 1.64-1.82 (m, 1H), 1.40 (m, 2H), 1.20 (m, 2H), 0.98-1.11 (m, 4H).

Example 4

Synthesis of Compound 4

Compound 4

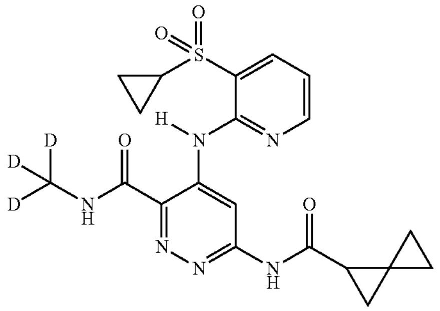

The steps are as follows:

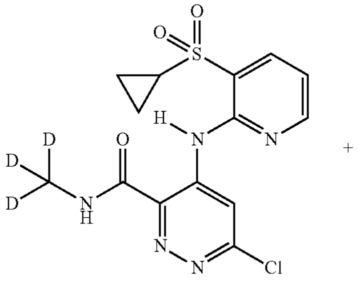

Compound 3c

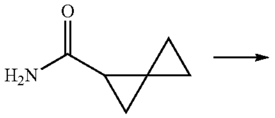

Compound 4a

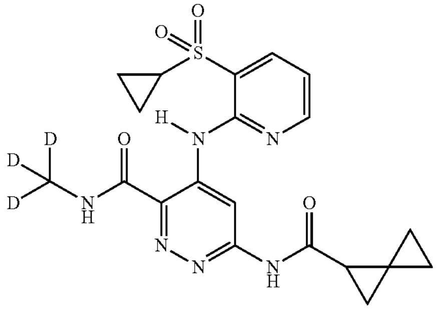 [SMILES: [2H]C([2H])([2H])NC(=O)c1nnc(NC(=O)C2CC23CC3)cc1Nc1ncccc1S(=O)(=O)C1CC1]

Compound 4

Compound 3c (0.21 g, 0.56 mmol, 1.0 eq), dioxane (20 ml), compound 4a (94 mg, 0.85 mmol, 1.5 eq), $Pd_2(dba)_3$ (0.05 g), and DPPF (0.06 g) were added into a 100 mL single-neck flask and replaced with nitrogen for 3 times. The mixture was stirred for 5 min, then added with $K_3PO_4$ aqueous solution (1 ml, 2 M, 3.6 eq), and replaced with nitrogen for 3 times. The mixture was reacted overnight at 112° C. TLC showed that the raw materials were not fully reacted. The reaction was concentrated, and separated by column chromatography to obtain compound 4 (a mixture of isomers) as pink powder (0.07 g, 3 mmol, yield 28%). MS-ESI: [M+1]+=446.5. 1H NMR (300 MHz, CDCl3): 12.4

(s, 1H), 9.64 (s, 1H), 8.86 (s, 1H), 8.61-8.64 (m, 1H), 8.14-8.23 (m, 2H), 7.12-7.17 (m, 1H), 2.86-2.92 (m, 1H), 2.18-2.22 (m, 1H), 1.66 (m, 1H), 1.55 (m, 1H), 1.40 (m, 2H), 1.0-1.13 (m, 6H).

Example 5

Synthesis of Compound 5

Compound 5

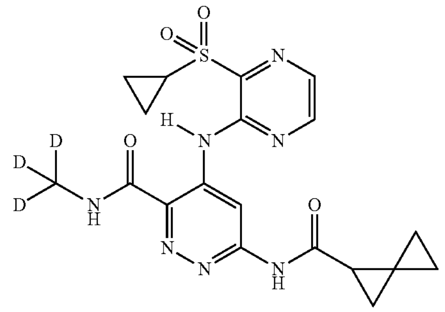

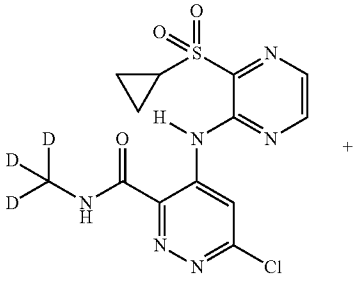

Compound 2c

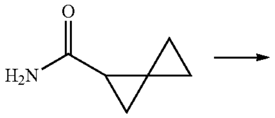

Compound 4a

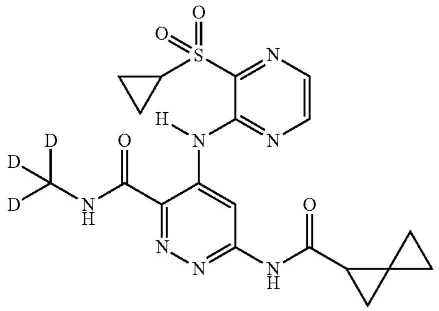 [SMILES: [2H]C([2H])([2H])NC(=O)c1nnc(NC(=O)C2CC23CC3)cc1Nc1nccnc1S(=O)(=O)C1CC1]

Compound 5

Compound 2c (0.25 g, 0.67 mmol, 1.0 eq), dioxane (20 ml), compound 4a (111 mg, 1 mmol, 1.5 eq), $Pd_2(dba)_3$ (0.05 g), and DPPF (0.06 g) were added into a 100 mL single-neck flask and replaced with nitrogen for 3 times. The mixture was stirred for 5 min, then added with $K_3PO_4$ aqueous solution (1 ml, 2M, 3.0 eq), and replaced with nitrogen for 3 times. The mixture was reacted overnight at 112° C. TLC showed that the raw materials were not fully reacted. The reaction was concentrated, separated by column chromatography and then underwent beating with methyl tert-butyl ether to obtain compound 5 (a mixture of isomers) as yellow powder (0.05 g, 0.112 mml, yield 16.7%). MS-ESI: [M+1]+=447.4. 1H NMR (300 MHz, CDCl3): 12.6 (s, 1H), 9.68 (s, 1H), 8.84 (s, 1H), 8.60 (d, 1H), 8.29 (d, 1H), 8.16 (s, 1H), 3.03-3.09 (m, 1H), 2.17-2.21 (m, 1H), 1.5-1.7 (m, 4H), 1.0-1.3 (m, 6H).

Example 6

Synthesis of Compound 6

Compound 6

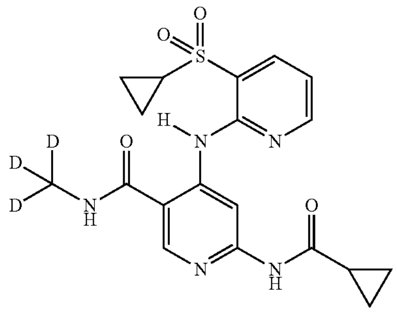

Step A

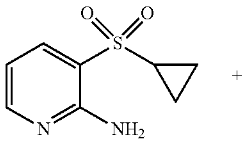

Compound 3b

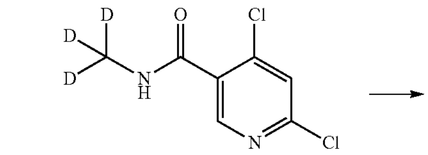

Compound 6a

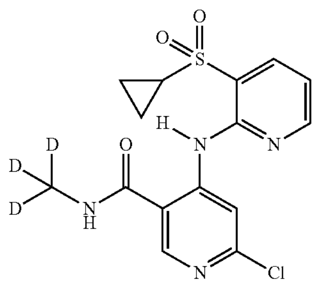

Compound 6b

Compound 3b (532 mg, 2.68 mmol, 1.0 eq), and DMF (20 ml) were added under nitrogen protection to a 200 mL three-necked flask. NaH (539 mg, 13.4 mmol, 60%) was added at 0-5° C. The mixture was stirred at room temperature for 30 mins. Compound 6a (700 mg, 3.38 mol, 1.2 eq) was further added under ice bath. The mixture was stirred at room temperature for 1 hour, and reacted at 50° C. for 3 h. The reaction was poured into a cold saturated ammonium chloride aqueous solution (100 ml), and extracted twice with ethyl acetate. The combined organic phase was washed twice with saturated salt water, dried over $Na_2SO_4$, concentrated, separated by column chromatography to obtain compound 6b as white powder (220 mg, 0.6 mmol, yield 22%). MS-ESI: [M+1]+=370.1. 1H NMR (400 MHz, CDCl3): 11.7 (s, 1H), 8.64 (s, 1H), 8.60 (s, 1H), 8.56 (m, 1H), 8.20 (m, 1H), 7.16 (m, 1H), 6.88 (m, 1H), 2.83-2.9 (m, 1H), 1.41-1.43 (m, 2H), 1.05-1.1 (m, 2H).

Step B

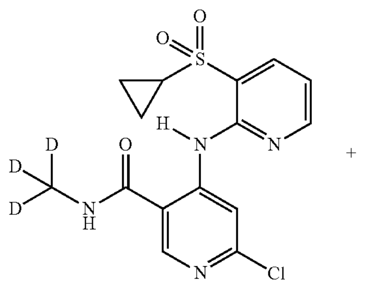

Compound 6b

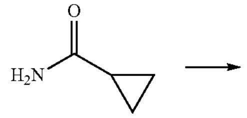

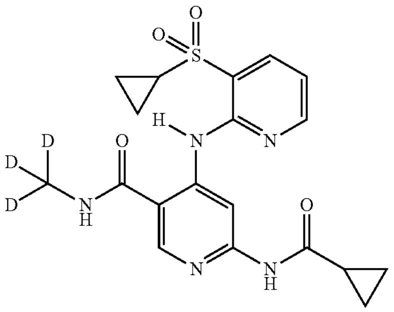

Compound 6

Compound 6b (200 mg, 0.51 mmol, 1.0 eq), dioxane (150 ml), cyclopropylformamide (230 mg, 2.7 mmol), $Pd_2(dba)_3$ (43 mg), and DPPF (94 mg) were added into a 100 mL single-neck flask and replaced with nitrogen for 3 times. The mixture was stirred for 5 min, then added with $Cs_2CO_3$ (355 mg, 1.08 mmol), and replaced with nitrogen for 3 times. The mixture was reacted overnight at 130° C. TLC showed that the raw materials were not fully reacted. The reaction was concentrated, and separated by column chromatography to obtain compound 6 as white powder (55 mg, 0.13 mmol, yield 25.5%). MS-ESI: [M+1]+=419.2. 1H NMR (400 MHz, d6-DMSO): 11.42 (s, 1H), 10.86 (s, 1H), 8.93 (s, 1H), 8.5-8.54 (m, 2H), 8.17-8.2 (m, 1H), 7.22-7.26 (m, 1H), 3.0 (m, 1H), 2.0 (m, 1H), 1.2 (m, 2H), 1.0 (m, 2H), 0.8 (m, 4H).

Test Example 1

The Inhibitory Effect of Compounds on the expression of pSTAT5 in CD3+ Cells Using FACS Detection 1. Experimental Materials and instruments:

1.1. Experimental reagents

DMSO, Sigma, Cat #D2650-100 ml, stored at room temperature.

Perm buffer III, BD Biosciences, Cat #558050, stored at 4° C.

Lyse/Fix buffer, BD Biosciences, Cat #558049, stored at room temperature.

EDTA, Invitrogen, Cat #15575-038, stored at room temperature.

PBS, Hyclone, Cat #SH30256.01, stored at 4° C.

PE Mouse Anti-Human CD3, BD Biosciences, Cat #555333, stored at 4° C.

Mouse anti-human Phospho-STATS (pY694) (Alexa Fluor® 647 Conjugate), BD Biosciences, Cat #562076, stored at 4° C.

IFN-α, Biolegend, Cat #592702

1.2 Experimental consumables

Microplate, 96 Well, PP, v-bottom, Greiner, Cat #GN651201-100EA.

5 ml polystyrene round bottom tube, FALCON, Cat #04318011.

96 square well storage plate, Thermo, Cat #AB-0661.

96-well plate, Corning, Cat #3599.

1.3 Instruments $CO_2$ cell incubator: MCO-15AC (Thermo)

Pipette: 0.2-10 μL, 20-200 μL, 200-1000 μL (Thermo)

Multichannel pipette: 0.2-10 μL, 5-50 μL, 20-300 μL (Raining)

Centrifuge: Thermo Centrifuge ST 40R; Thermo LEGEND Micro 21R

Water system: Millipore Milli-Q Reference system

Freezer: Haier ultralow temperature freezer

Haier 4 centigrade refrigerator

Haier −20 centigrade freezer

Vortex: EARTH REQUIRED

Plate Shaker: QI LIN BEI ER; MH-2

Flow Cytometer: BD FACSVerse™ Flow Cytometer

2 Experimental method:

2.1 Compound Dilution

1) On the day of experiment, the compound was prepared into a 10 mM solution with DMSO, diluted to 1.5 mM with DMSO, and then diluted to 8 gradient concentrations with 3-fold dilutions.

2) 5 μl of diluted compound was transferred into 120 ul of DPBS solution with 0.1% BSA.

3) Positive and negative control groups were set up, with an addition of 0.5% DMSO to the positive and negative control groups.

2.2 Experimental procedure 1) 67.5 ul of fresh human whole blood was added to the 96-well cell culture plate.

2) 3.5 ul of diluted compound was added and mixed well.

3) Incubating in a 37° C. incubator for 60 minutes.

4) IFN-α was diluted in DPBS containing 0.1% BSA to 400 ng/ml, and PE anti-hCD3 antibody was diluted in DPBS containing 0.1% BSA to 5-fold. After the above 60-minute incubation, diluted PE anti-hCD3 antibody was added at 5 ul per well and diluted IFN-α was added at 4 ul per well, i.e., the final concentration of IFN-α per well was 20 ng/ml.

5) Incubating in a 37° C. incubator for 15 minutes.

6) All cells were transferred to a 96-well deep well plate and 1 ml of 37° C. preheated lysis/fix buffer was added.

7) Incubating at 37° C. in dark for 10 minutes.

8) Centrifuging at 600 g for 5 minutes and then the supernatant was discarded. Washing by adding 1 ml PBS for twice and centrifuging.

9) 1 ml of Perm buffer III was added to cell precipitation.

10) Incubating at 37° C. in dark for 30 minutes.

11) Centrifuging at 600 g for 5 minutes and then the supernatant was discarded. Washing by adding 1 ml PBS for twice and centrifuging.

12) APC anti-human pSTAT5 antibody was diluted in staining buffer, and then added to cell wells at 100 ul per well and mixed well.

13) Incubating at room temperature for 40 minutes.

14) Staining buffer was added and washed twice, 1 ml for each well, centrifuging at 600 g for 5 minutes.

15) After discarding the supernatant, the cell precipitation was resuspended in 300 ul of staining buffer.

16) Sample loading and analysing in a flow cytometer. The IC50 of the samples to be tested was obtained from the calculation and the results were shown in Table 1.

TABLE 1

| Compound No. | IFN-α/pSTAT5 IC50(nM) |
|---|---|
| 1 | 2800 |
| 2 | 867 |
| 3 | 64 |
| 4 | 168 |
| 5 | 2111 |
| 6 | 128 |

Test Example 2

Comparison of Selectivity on JAK Family

1. Experimental method 1.1. Pseudokinase (JH2) experiment operation was as follows:

1.1.1. The compound was dissolved with DMSO to a storage concentration of 10 mM.

1.1.2. A compound concentration of 200 times the final concentration was prepared in a compound dilution plate, which was diluted from the highest concentration point with a total of 4 concentration points using the 27 times dilution method, and then transferred to the Echo plate.

1.1.3. The compound was flushed from the Echo plate to the 384 well experimental plate using an Echo instrument, thereby obtaining a total of 11 concentration points of the compound with three-fold dilution matrix.

1.1.4. 5 ul of TYK2-JH2 or JAK1-JH2 pseudokinase, 3 times the final concentration, was added to the 384-well experimental plate.

1.1.5. 5 ul of Tb, 3 times the final concentration, was added to the 384-well experimental plate.

1.1.6. 5 ul of Tracer, 3 times the final concentration, was added to the 384-well experimental plate.

1.1.7. Centrifuging for 30 seconds and incubating at room temperature for 60 minutes.

1.1.8. The fluorescence ratio of 520 nm to 495 nm was read using Envision Microplate Reader (PerkinElmer).

1.2. Kinase (JH1) experiment operation was as follows:

1.2.1. The compound was dissolved with DMSO to a storage concentration of 10 mM.

1.2.2. A compound concentration of 100 times the final concentration was prepared in a compound dilution plate, which was diluted from the highest concentration point with a total of 4 concentration points using the 27 times dilution method, and then transferred to the Echo plate.

1.2.3. The compound was flushed from the Echo plate to the 384 experimental plate using an Echo instrument, thereby obtaining a total of 11 concentration points of the compound with three-fold dilution matrix.

1.2.4. A kinase working solution with a concentration twice the final concentration was prepared, and then added to a 384-well experimental plate at 5 ul per well. The compound and the kinase were incubated at room temperature for 15 minutes.

1.2.5. Sul of substrate (containing ATP), twice the final concentration, was added to the 384 well plate.

1.2.6. Incubating at room temperature for 45 minutes.

1.2.7. The detection reagent mixture was added to the 384-well plate, centrifuged for 30 seconds, and incubated at room temperature for 60 minutes.

1.2.8. The fluorescence ratio at 665 nm and 615 nm were read using Envision Microplate Reader (PerkinElmer).

1.3. Data analysis:

1.3.1. XL-Fit software was used for data analysis, IC50 of compounds was obtained by calculation, see Table 2.

TABLE 2

| Compound No. | TYK2(JH1) | TYK2(JH2) | JAK1(JH1) | JAK1(JH2) | JAK2(JH1) | JAK3(JH1) |
|---|---|---|---|---|---|---|
| 3 | 4313.5 nM | 0.32 nM | 3185.5 nM | 53.1 nM | 2812.9 nM | 2378.3 nM |
| $IC50_{Other}/IC50_{TYK2\text{-}JH2}$ | 13480 | 1 | 9955 | 166 | 8790 | 7432 |

All documents mentioned in the present invention are cited as references in this application, just as each document is individually cited as a reference. In addition, it should be understood that, after reading the above teaching content of the present invention, those skilled in the art can make various changes or modifications to the present invention, and these equivalent forms also fall within the scope defined by the appended claims of the present application.

The invention claimed is:

1. A heterocyclic compound or pharmaceutically acceptable salts thereof, wherein the compound is as represented by formula I;

(I)

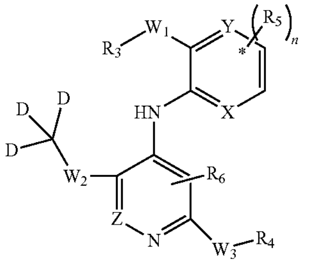

wherein,

X and Y are each independently $CR_5$ or N;

Z is $CR_6$ or N;

$W_1$ and $W_2$ are each independently divalent group selected from the group consisting of O, S, $SO_2$, CO, $NR_7CO$, $CONR_7$;

$W_3$ is a divalent group selected from the group consisting of CO, $NR_7$, $NR_7CO$, $CONR_7$;

$R_3$ is substituted or unsubstituted $C_{3-6}$ cycloalkyl;

$R_4$ is selected from the group consisting of substituted or unsubstituted $C_{1-6}$ alkyl, substituted or unsubstituted $C_{3-6}$ cycloalkyl; and $R_4$ is optionally further substituted with $R_1$ and $R_2$;

$R_1$ and $R_2$ are each independently selected from the group consisting of H, substituted or unsubstituted $C_{1-6}$ alkyl; or, $R_1$ and $R_2$ together with the carbon to which they are attached form substituted or unsubstituted $C_{3-6}$ cycloalkyl;

$R_5$, $R_6$ and $R_7$ are each independently selected from the group consisting of H, substituted or unsubstituted $C_{1-4}$alkyl;

n=1 or 2;

unless otherwise specified, said substituted means that one or more of hydrogen atoms in the group are substituted with substituents selected from the group consisting of halogen, $C_{1-4}$ alkyl, and $C_{1-4}$ haloalkyl.

2. The heterocyclic compound of claim 1, wherein the heterocyclic compound is as shown in formula IA;

(IA)

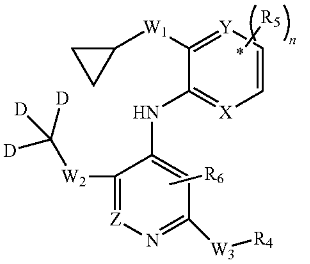

wherein, X, Y, Z, $W_1$, $W_2$, $W_3$, $R_4$, $R_5$ and n are as defined in claim 1.

3. The heterocyclic compound of claim 1, wherein the heterocyclic compound is as shown in formula II;

(II)

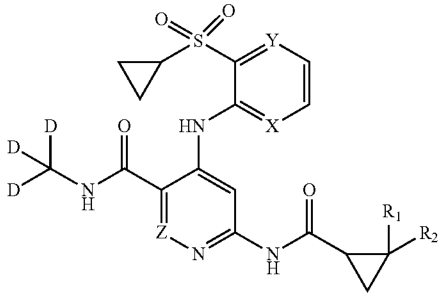

wherein,

X and Y are each independently $CR_5$ or N;

Z is $CR_6$ or N;

$R_1$ and $R_2$ are each independently selected from the group consisting of H, substituted or unsubstituted $C_{1-6}$ alkyl group; or, $R_1$ and $R_2$ together with the carbon to which they are attached form substituted or unsubstituted $C_{3-6}$ cycloalkyl;

$R_5$ and $R_6$ are each independently selected from the group consisting of H, substituted or unsubstituted $C_{1-4}$alkyl;

unless otherwise specified, said substituted means that one or more of hydrogen atoms in the group are substituted with substituent selected from the group consisting of halogen, $C_{1-4}$ alkyl, and $C_{1-4}$ haloalkyl.

4. The heterocyclic compound of claim 1, wherein, X is N, Y is $CR_5$, and Z is N.

5. The heterocyclic compound of claim 1, wherein, the compound is a compound selected from the group consisting of Compound 1, Compound 2, Compound 3, Compound 4, Compound 5, and Compound 6, as shown in Table A:

TABLE A

| | |
|---|---|
| 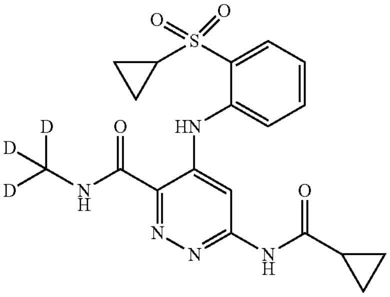 | Compound 1 |
| 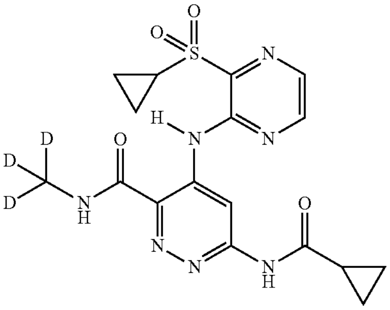 | Compound 2 |

TABLE A-continued

Compound 3

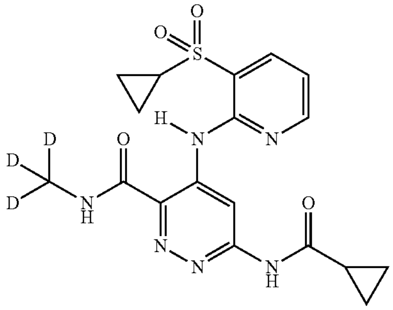

Compound 4

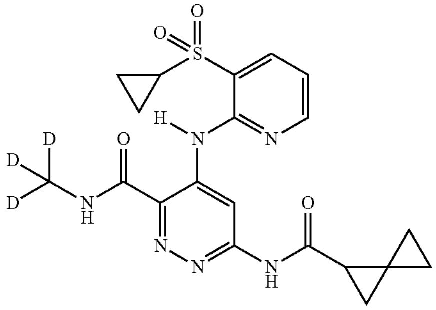

Compound 5

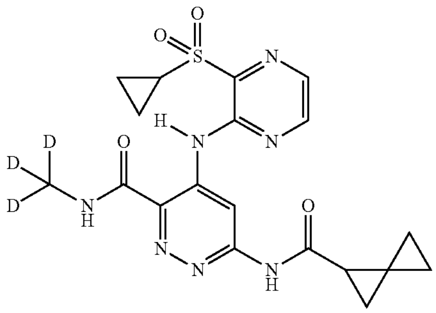

and

Compound 6

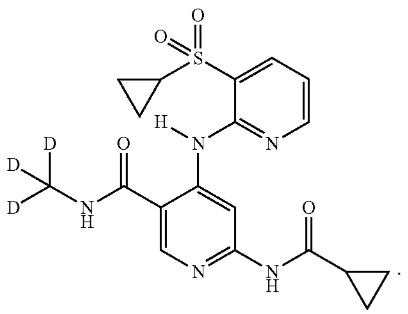 [SMILES: [2H]C([2H])([2H])NC(=O)c1cnc(NC(=O)C2CC2)cc1Nc1ncccc1S(=O)(=O)C1CC1]

6. An intermediate for preparing the heterocyclic compound of claim 1, wherein the intermediate is as shown in formula III, formula IIIA, formula IIIB, formula IIIC, or formula IV:

(III)

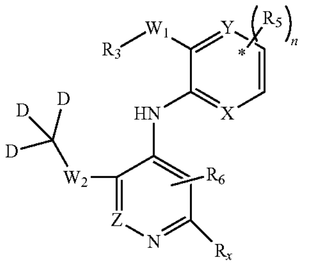

(IIIA)

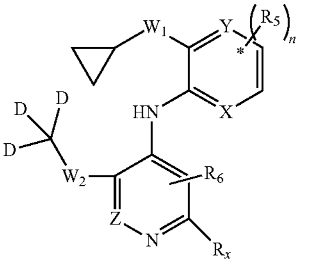

(IIIB)

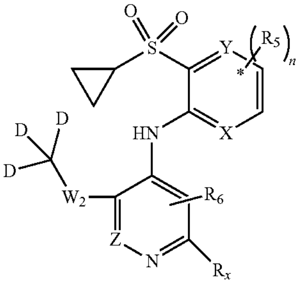

or (IV)

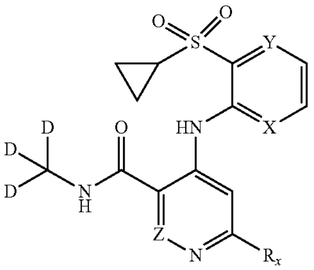

wherein, $R_x$ is halo; X, Y, Z, $W_1$, $W_2$, $W_3$, $R_1$, $R_2$, $R_3$, $R_4$, $R_5$, $R_6$, $R_7$ and n are as defined in claim 1.

7. A pharmaceutical composition, comprising
the heterocylic compound of claim 1 or a pharmaceutically acceptable salt thereof,
and a pharmaceutically acceptable carrier or excipient.

8. A method for treating or preventing TYK2 mediated diseases and/or inhibiting TYK2, comprising administering the heterocyclic compound of claim 1, or a pharmaceutically acceptable salt thereof.

9. The method of claim 8, wherein the TYK2-JH2-mediated diseases are selected from the group consisting of inflammation, autoimmune diseases, or combinations thereof.

10. A method of selectively inhibiting TYK2, comprising: contacting the subject with the heterocyclic compound of claim 1, thereby inhibiting the activity of TYK2-JH2 in the subject.

* * * * *